(12) United States Patent
Schaeffer et al.

(10) Patent No.: US 9,597,152 B2
(45) Date of Patent: Mar. 21, 2017

(54) CONTROL HANDLES FOR MEDICAL DEVICES

(75) Inventors: Darin Schaeffer, Bloomington, IN (US); Pamela Ridgley, Bloomington, IN (US); Daniel McCarthy, Chicago, IL (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 0 days.

(21) Appl. No.: 13/608,002

(22) Filed: Sep. 10, 2012

(65) Prior Publication Data

US 2013/0237968 A1 Sep. 12, 2013

Related U.S. Application Data

(60) Provisional application No. 61/533,190, filed on Sep. 10, 2011.

(51) Int. Cl.
| | | |
|---|---|---|
| *A61B 17/22* | (2006.01) | |
| *A61B 17/00* | (2006.01) | |
| *A61B 18/26* | (2006.01) | |
| *A61B 17/221* | (2006.01) | |
| *A61B 17/34* | (2006.01) | |

(52) U.S. Cl.
CPC .............. *A61B 18/26* (2013.01); *A61B 17/22* (2013.01); *A61B 17/221* (2013.01); *A61B 17/22012* (2013.01); *A61B 2017/00469* (2013.01); *A61B 2017/3445* (2013.01); *A61B 2090/062* (2016.02)

(58) Field of Classification Search
CPC ............ A61B 18/26; A61B 2019/5437; A61B 17/22012

USPC ....................................................... 606/2.5, 1
See application file for complete search history.

(56) References Cited

U.S. PATENT DOCUMENTS

| | | |
|---|---|---|
| 4,589,415 A | 5/1986 | Haaga |
| 4,721,107 A | 1/1988 | Bolg et al. |
| 4,726,369 A | 2/1988 | Mar |
| 4,774,947 A | 10/1988 | Falk et al. |
| 4,823,793 A | 4/1989 | Angulo et al. |
| 4,858,810 A | 8/1989 | Intlekofer et al. |
| 4,960,108 A | 10/1990 | Reichel et al. |
| 5,045,061 A | 9/1991 | Seifert et al. |
| 5,065,761 A | 11/1991 | Pell |

(Continued)

FOREIGN PATENT DOCUMENTS

| | | |
|---|---|---|
| EP | 1528893 | 7/2009 |
| EP | 2359776 | 8/2011 |
| WO | WO2005094936 | 10/2005 |

OTHER PUBLICATIONS

European Patent Office, Partial European Search Report, for European Application No. 13160954.7 mailed Jun. 6, 2013, p. 1-5.

(Continued)

*Primary Examiner* — William Thomson
*Assistant Examiner* — Sebastian X Lukjan
(74) *Attorney, Agent, or Firm* — Buchanan Nipper

(57) ABSTRACT

Various medical devices and methods of treatment are described herein. For example, various detachable control handle configurations for inclusion with a medical device, such as a lithotripter, are described. In another example, various probe configurations are described herein. Furthermore, various methods of treatment using a control handle are described herein.

11 Claims, 9 Drawing Sheets

(56) References Cited

U.S. PATENT DOCUMENTS

| | | | |
|---|---|---|---|
| 5,137,288 | A | 8/1992 | Starkey et al. |
| 5,159,861 | A | 11/1992 | Anderson |
| 5,161,534 | A | 11/1992 | Berthiaume |
| 5,163,421 | A | 11/1992 | Bernstein et al. |
| 5,163,903 | A | 11/1992 | Crittenden et al. |
| 5,197,968 | A | 3/1993 | Clement |
| 5,199,417 | A | 4/1993 | Muller et al. |
| 5,209,719 | A | 5/1993 | Baruch et al. |
| 5,219,332 | A | 6/1993 | Nelson et al. |
| 5,242,454 | A * | 9/1993 | Gundlach ............ A61B 18/26 128/898 |
| 5,273,052 | A | 12/1993 | Kraus et al. |
| 5,281,230 | A | 1/1994 | Heidmueller |
| 5,290,294 | A | 3/1994 | Cox et al. |
| 5,312,418 | A | 5/1994 | Bonnet |
| 5,325,868 | A | 7/1994 | Kimmelstiel |
| 5,392,778 | A | 2/1995 | Horzewski |
| 5,425,735 | A | 6/1995 | Rosen et al. |
| 5,484,433 | A | 1/1996 | Taylor et al. |
| 5,540,656 | A | 7/1996 | Pflueger et al. |
| 5,792,145 | A | 8/1998 | Bates et al. |
| 5,851,189 | A | 12/1998 | Forber |
| 5,868,756 | A | 2/1999 | Henry et al. |
| 5,906,623 | A * | 5/1999 | Peterson ................. 606/128 |
| 5,944,728 | A | 8/1999 | Bates |
| 5,954,670 | A | 9/1999 | Baker |
| 6,004,330 | A | 12/1999 | Middleman et al. |
| 6,007,560 | A * | 12/1999 | Gottlieb et al. ............ 606/205 |
| 6,030,349 | A | 2/2000 | Wilson et al. |
| 6,033,414 | A | 3/2000 | Tockman et al. |
| 6,059,796 | A | 5/2000 | Bilitz et al. |
| 6,093,748 | A | 7/2000 | Ahluwalia et al. |
| 6,193,730 | B1 | 2/2001 | Beland |
| 6,217,588 | B1 | 4/2001 | Jerger et al. |
| 6,238,389 | B1 | 5/2001 | Paddock et al. |
| 6,241,744 | B1 | 6/2001 | Imran et al. |
| 6,264,664 | B1 | 7/2001 | Avellanet |
| 6,352,534 | B1 | 3/2002 | Paddock et al. |
| 6,440,123 | B1 | 8/2002 | Engel |
| 6,458,137 | B1 | 10/2002 | Klint |
| 6,482,203 | B2 | 11/2002 | Paddock et al. |
| 6,533,772 | B1 | 3/2003 | Sherts et al. |
| 6,613,014 | B1 * | 9/2003 | Chi ......................... 604/93.01 |
| 6,645,223 | B2 | 11/2003 | Boyle et al. |
| 6,660,013 | B2 | 12/2003 | Rabiner et al. |
| 6,673,080 | B2 | 1/2004 | Reynolds et al. |
| 6,695,834 | B2 | 2/2004 | Gellman et al. |
| 6,866,670 | B2 | 3/2005 | Rabiner et al. |
| 7,087,061 | B2 | 8/2006 | Chernenko et al. |
| 7,144,378 | B2 | 12/2006 | Arnott |
| 7,470,274 | B2 | 12/2008 | Lebet |
| 7,682,366 | B2 | 3/2010 | Sakurai et al. |
| 7,717,865 | B2 | 5/2010 | Boutillette et al. |
| 7,831,297 | B2 | 11/2010 | Opie et al. |
| 7,909,821 | B2 | 3/2011 | Paddock et al. |
| 7,914,540 | B2 | 3/2011 | Schwartz et al. |
| 7,972,282 | B2 | 7/2011 | Clark et al. |
| 7,993,329 | B2 | 8/2011 | Howell et al. |
| 8,038,628 | B2 | 10/2011 | von Malmborg et al. |
| 8,147,481 | B2 | 4/2012 | Whittaker et al. |
| 8,496,603 | B2 | 7/2013 | Mamourian |
| 2001/0016712 | A1 | 8/2001 | Hamilton |
| 2003/0069522 | A1 | 4/2003 | Jacobsen et al. |
| 2003/0176873 | A1 | 9/2003 | Chernenko et al. |
| 2004/0039372 | A1 | 2/2004 | Carmody |
| 2004/0172116 | A1 | 9/2004 | Seifert et al. |
| 2004/0215108 | A1 | 10/2004 | Windheuser |
| 2004/0225283 | A1 * | 11/2004 | Nahleili ............... A61B 18/22 606/2 |
| 2005/0070820 | A1 | 3/2005 | Boutillette et al. |
| 2005/0288655 | A1 | 12/2005 | Root et al. |
| 2006/0229496 | A1 | 10/2006 | Windheuser et al. |
| 2007/0004991 | A1 | 1/2007 | Shelton |
| 2007/0010849 | A1 | 1/2007 | Balgobin et al. |
| 2007/0016166 | A1 | 1/2007 | Thistle |
| 2007/0021754 | A1 | 1/2007 | Chernenko et al. |
| 2007/0179486 | A1 | 8/2007 | Welch et al. |
| 2008/0103481 | A1 * | 5/2008 | Vogel et al. ................. 604/514 |
| 2008/0132906 | A1 | 6/2008 | Rasmussen |
| 2008/0147110 | A1 | 6/2008 | Wijeratne |
| 2008/0312671 | A1 | 12/2008 | Riles et al. |
| 2009/0118741 | A1 | 5/2009 | Lebet |
| 2009/0124899 | A1 | 5/2009 | Jacobs et al. |
| 2009/0124934 | A1 | 5/2009 | Rabbitte et al. |
| 2009/0292278 | A1 * | 11/2009 | Lewinsky et al. ............. 606/16 |
| 2010/0036294 | A1 | 2/2010 | Mantell et al. |
| 2010/0100103 | A1 | 4/2010 | Haskal et al. |
| 2010/0211006 | A1 | 8/2010 | Schmidt-Sorensen |
| 2011/0112507 | A1 | 5/2011 | Linderman et al. |
| 2011/0245841 | A1 * | 10/2011 | Shohat et al. ................ 606/127 |
| 2012/0136425 | A1 | 5/2012 | Orr |
| 2013/0018359 | A1 | 1/2013 | Coyle |
| 2013/0035749 | A1 | 2/2013 | Farag |
| 2013/0103001 | A1 | 4/2013 | BenMaamer et al. |
| 2013/0303330 | A1 | 11/2013 | Stevens et al. |

OTHER PUBLICATIONS

European Patent Office, Extended European Search Report for application No. 13160954.7 mailed Sep. 26, 2013, p. 1-9.

International Searching Authority, The International Search Report and the Written Opinion of the International Searching Authority for International Application No. PCT/US2012/054374 mailed Dec. 12, 2012.

International Bureau of WIPO. International Preliminary Report on Patentability and Written Opinion, for International Application No. PCT/US2012/054374. Mar. 20, 2014. p. 1-8.

* cited by examiner

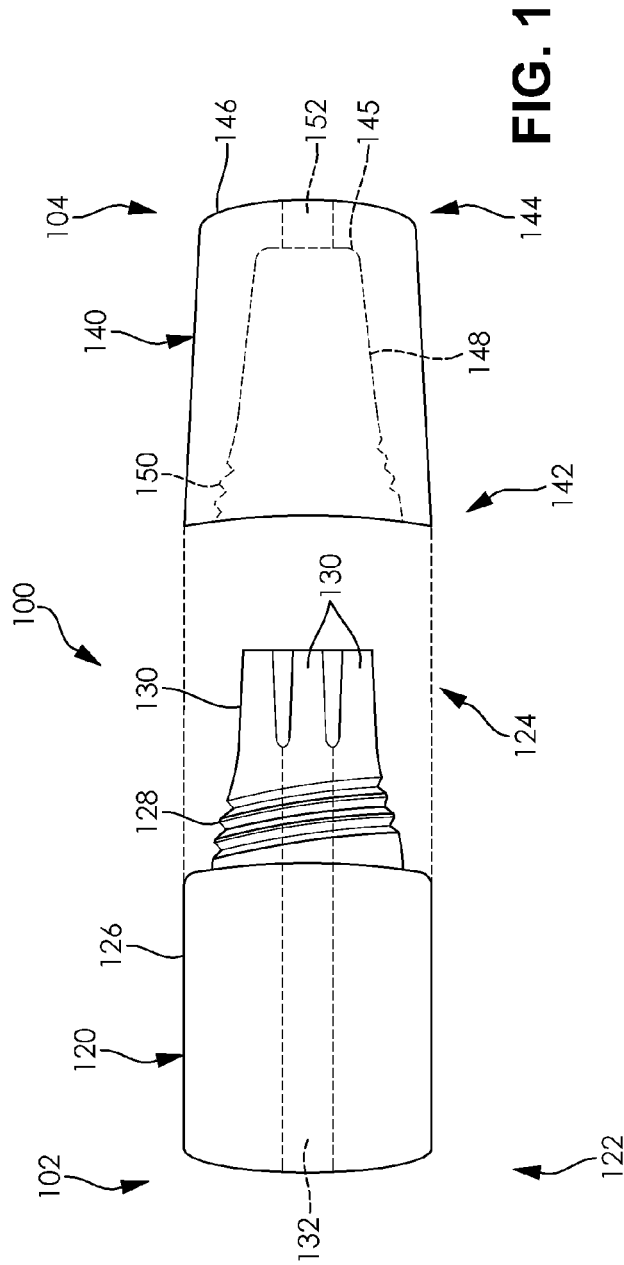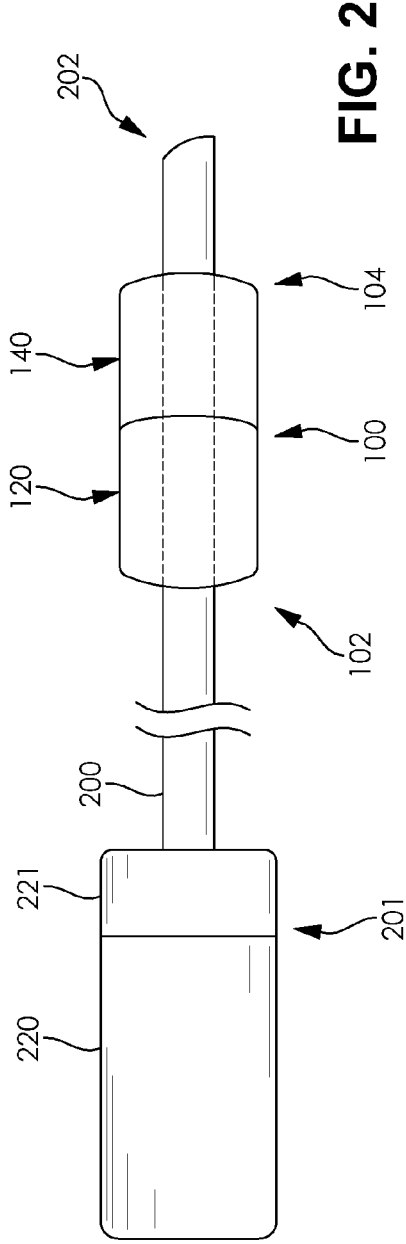

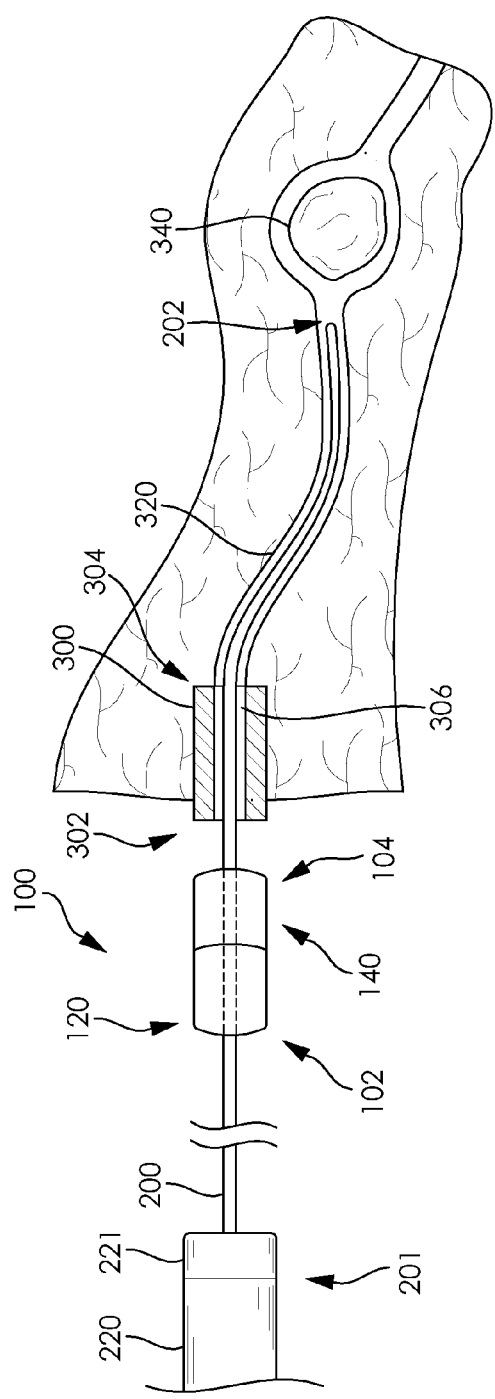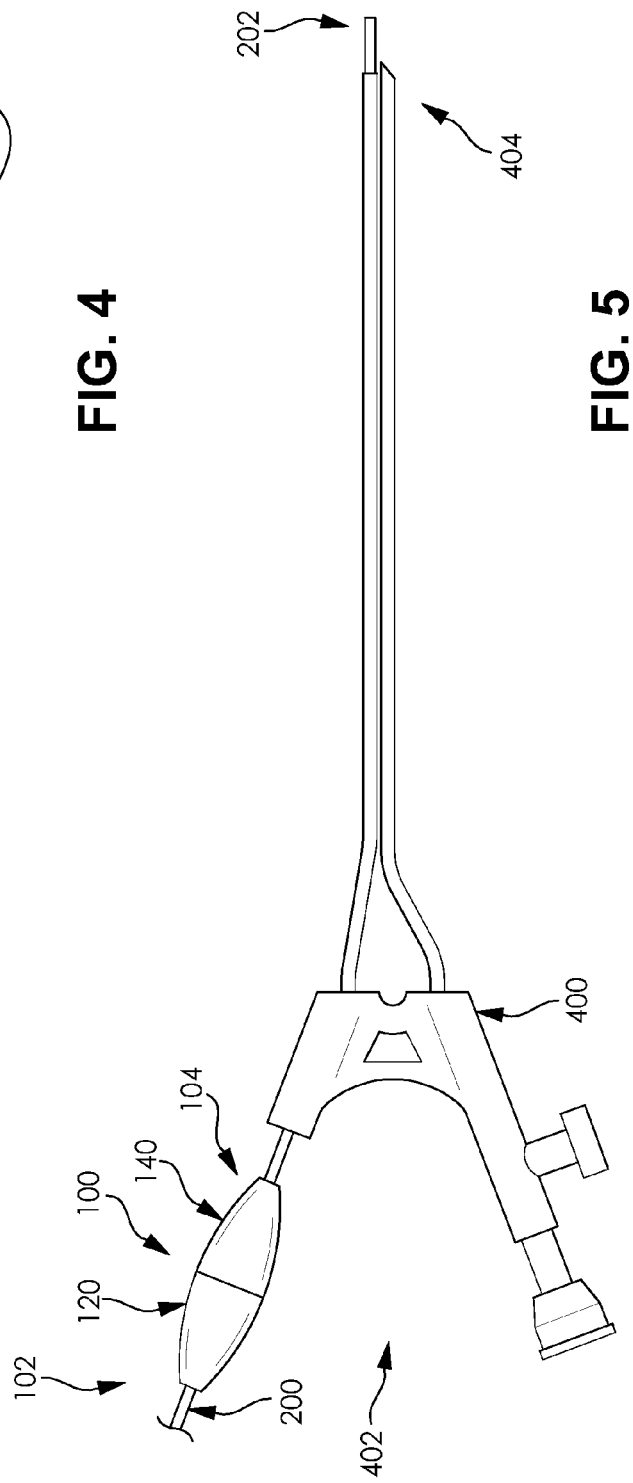

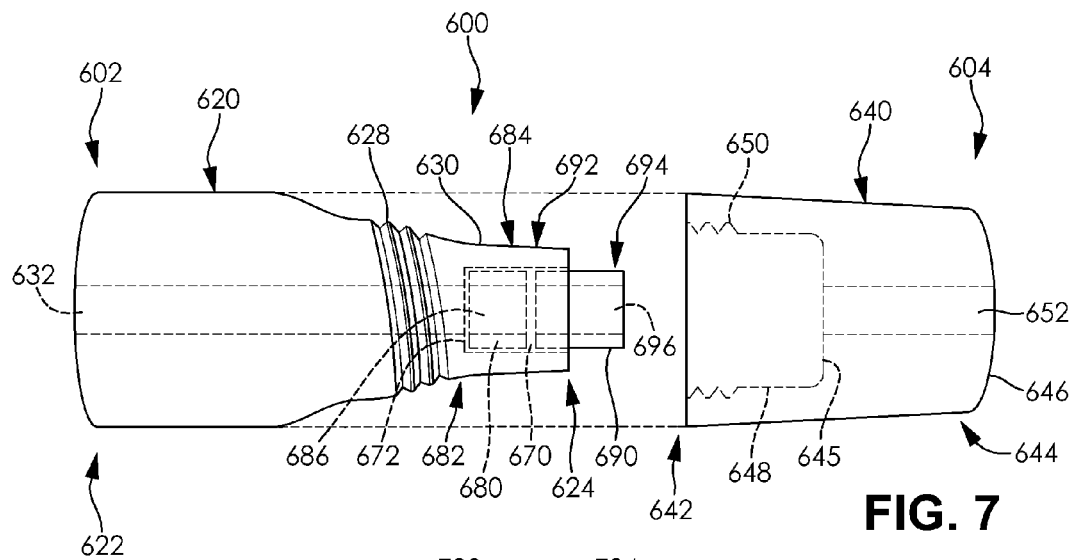
FIG. 7
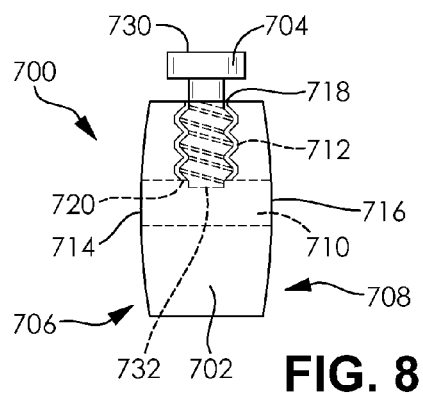
FIG. 8
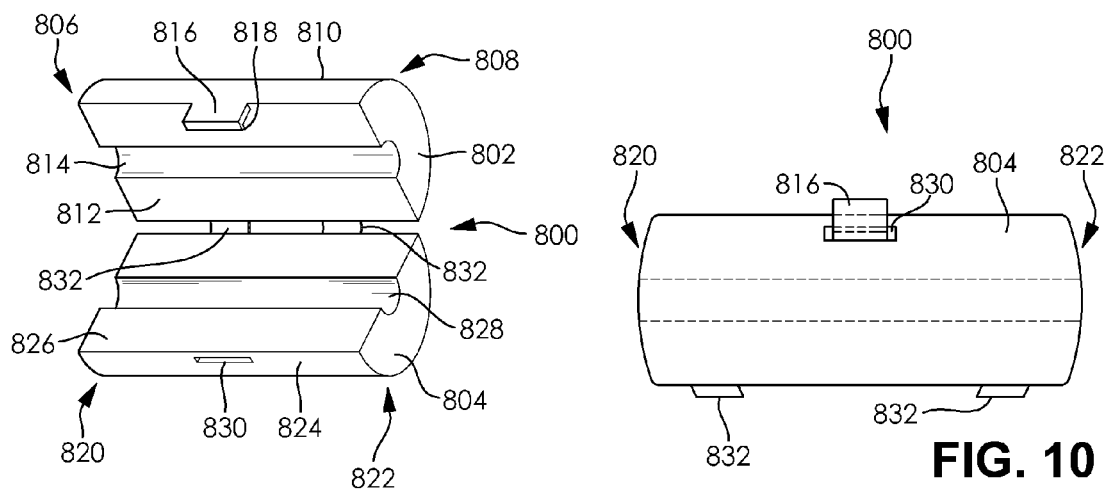
FIG. 9
FIG. 10

CONTROL HANDLES FOR MEDICAL DEVICES

CROSS REFERENCE TO RELATED APPLICATIONS

This application claims the benefit of U.S. Provisional Application Ser. No. 61/533,190, filed on Sep. 10, 2011. The entire contents of this related application is incorporated into this disclosure by reference.

FIELD

The disclosure relates generally to medical devices. Particular embodiments disclosed herein relate to control handles for medical devices, such as lithotripters. The disclosure also relates to methods of treatment.

BACKGROUND

It is sometimes necessary to remove one or more stones located within a bodily passage. For example, to treat salivary duct stones, ureteral stones, and kidney stones a lithotripsy may be performed in which a rigid probe attached to a firing handle is inserted into the bodily passage to fragment the stone. The procedure is accomplished by advancing the probe through a sheath disposed in the bodily passage, or the working channel of a scope, until the probe comes into contact with the stone. The firing handle is then activated to fire the probe and fragment the stone for removal.

Current lithotripters do not provide a mechanism that allows for fine motor control over the probe during the performance of a procedure. Rather, gross motor control is utilized to adjust the length of the probe disposed in the bodily passage by either manipulating the firing handle or grasping a portion of the probe itself, which is smooth and has a small diameter. The lack of fine motor control over the probe during the performance of a procedure decreases the efficiency of the procedure and increases the likelihood of the probe perforating the wall of the bodily passage and/or causing tissue damage.

Therefore, a need exists for improved medical devices and methods for performing a procedure, such as lithotripsy.

SUMMARY

Various exemplary methods of treatment are described herein.

An exemplary method of removing a stone disposed within a salivary duct having a salivary duct opening comprises a step of positioning a control handle on a medical device having a proximal end and a distal end. Another step comprises releasably attaching the control handle to the medical device. Another step comprises inserting the distal end of the medical device through said salivary duct opening such that the distal end of the medical device is disposed distal to said salivary duct opening and in said salivary duct. Another step comprises navigating the distal end of the medical device through said salivary duct and towards a point of treatment. Another step comprises contacting the distal end of the medical device with said stone disposed in said salivary duct. Another step comprises performing treatment using the medical device. Another step comprises withdrawing the medical device from said salivary duct.

Another exemplary method of removing a stone disposed within a salivary duct having a salivary duct opening comprises a step of positioning a control handle on a medical device having a proximal end and a distal end. Another step comprises releasably attaching the control handle to the medical device. Another step comprises inserting the distal end of the medical device into a lumen defined by a scope having a proximal end and a distal end such that the distal end of the medical device is disposed distal to the distal end of the scope. The lumen of the scope extends between an opening at the proximal end of the scope and an opening at the distal end of the scope. Another step comprises inserting the distal end of the medical device through said salivary duct opening such that the distal end of the medical device is disposed distal to said salivary duct opening and in said salivary duct. Another step comprises inserting the distal end of the scope through said salivary duct opening such that the distal end of the scope is disposed distal to said salivary duct opening and in said salivary duct. Another step comprises navigating the distal end of the medical device through said salivary duct and towards a point of treatment. Another step comprises contacting the distal end of the medical device with said stone disposed in said salivary duct. Another step comprises performing treatment using the medical device. Another step comprises withdrawing the medical device from said salivary duct.

Various exemplary medical devices are also described herein.

An exemplary control handle comprises a first portion, a second portion, and a compressible member. The first portion has a proximal end, a distal end, a first shaft, a projection, and defines a recess and an aperture. The shaft extends from the proximal end towards the distal end of the first portion. The projection extends from a location between the proximal end and the distal end to the distal end of the first portion. The recess extends into the projection from the distal end of the first portion towards the proximal end of the first portion to a recess base. The aperture extends from a first opening defined on the proximal end of the first portion to a second opening defined on the recess base. The second portion has a proximal end, a distal end, a second shaft, and defines a recess and an aperture. The second shaft extends from the proximal end to the distal end of the second portion. The recess extends into second shaft and from the proximal end towards the distal end of the second portion to a recess base. The aperture extends from a first opening defined on the recess base of the second portion to a second opening defined on the distal end of the second portion. The compressible member has a proximal end and a distal end. A portion of the compressible member is disposed within one of the recess defined by the first portion or the recess defined by the second portion. The first portion is adapted to be releasably attached to the second portion. The projection is adapted to be received by the recess defined by the second portion. The control handle is moveable between a first configuration and a second configuration. In the first configuration, the projection is free of the recess of the second portion. In the second configuration, the projection is disposed within the recess of the second portion and the first portion is releasably attached to the second portion.

Additional understanding of the exemplary medical devices and methods can be obtained by reviewing the detailed description, below, and the appended drawings.

BRIEF DESCRIPTION OF THE DRAWINGS

FIG. 1 is an exploded side view of an exemplary control handle.

FIG. 2 is a side view of an exemplary control handle disposed on a probe.

FIG. 4 is a partial cross sectional view of the exemplary control handle illustrated in FIG. 1 disposed on a probe that has been advanced through a sheath disposed in the opening of a salivary duct.

FIG. 5 is a side view of the exemplary control handle illustrated in FIG. 1 disposed on a probe that has been advanced through a scope.

FIG. 7 is an exploded side view of a second exemplary control handle.

FIG. 8 is a side view of a third exemplary control handle.

FIG. 9 is a perspective view of a fourth exemplary control handle in a first configuration.

FIG. 10 is a side view of the exemplary control handle illustrated in FIG. 9 in a second configuration.

DETAILED DESCRIPTION

Figure 3:
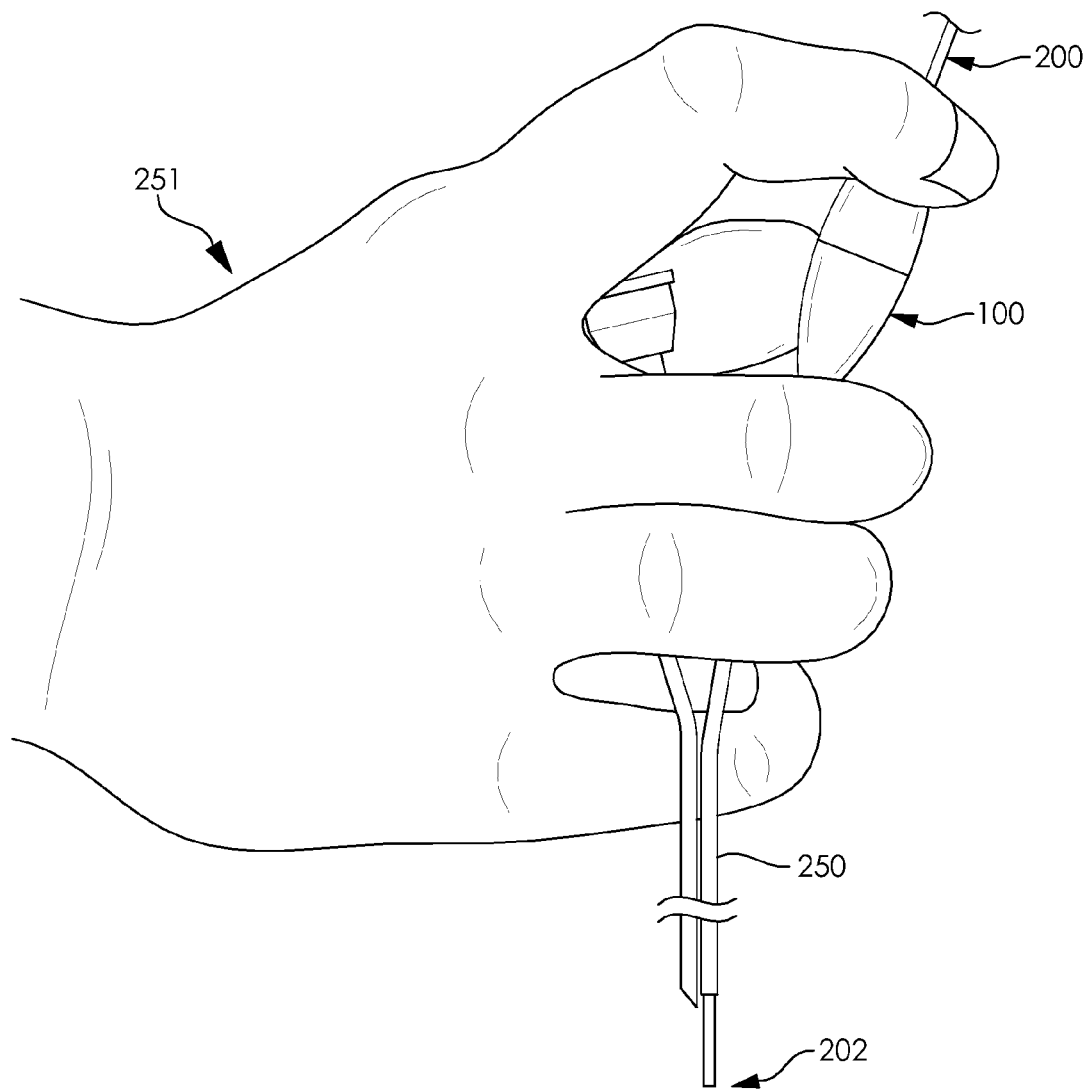
FIG. 3 is a side view of an exemplary control handle disposed on a probe that has been advanced through a scope.

The following detailed description and the appended drawings describe and illustrate various exemplary medical devices and methods. The description and drawings are exemplary in nature and are provided to enable one skilled in the art to make and use one or more exemplary medical devices, and/or practice one or more exemplary methods. They are not intended to limit the scope of the claims in any manner.

The use of "e.g.," "etc.," "for instance," "in example," and "or" and grammatically related terms indicates non-exclusive alternatives without limitation, unless otherwise noted. The use of "optionally" and grammatically related terms means that the subsequently described element, event, or circumstance may or may not be present/occur, and that the description includes instances where said element, event, or circumstance occurs and instances where it does not. As used herein, the terms "proximal" and "distal" are used to describe opposing axial ends of the particular elements or features being described. The term "bodily passage" refers to any passage within the body of an animal, including, but not limited to, humans, and includes elongate passages. The term "salivary duct" refers to the parotid ducts, submandibular ducts, and/or sublingual ducts. The term "exemplary" refers to "an example of" and is not intended to convey a meaning of an ideal or preferred embodiment.

FIG. 1 illustrates an exemplary detachable control handle 100 comprising a proximal end 102, a distal end 104, a first portion 120, and a second portion 140. The control handle 100 has a first configuration and a second configuration, each described in more detail below.

The first portion 120 comprises a proximal end 122, distal end 124, shaft 126, threaded portion 128, and one or more projections 130. The shaft 126 extends from the proximal end 122 towards the distal end 124. The threaded portion 128 extends from distal end of the shaft 126 towards the distal end 124. The one or more projections 130 extend from a location between the proximal end 122 and the distal end 124 of the first portion 120 to the distal end 124 of the first portion 120. The one or more projections 130 extend about the entirety, or a portion of, the circumference of the distal end of the threaded portion 128 to the distal end 124 of the first portion 120. In an example, the one or more projections 130 form a collet configuration that extends from the distal end of the threaded portion 128 to the distal end 124 of the first portion 120. The one or more projections 130 can optionally comprise one or more teeth and or ridges on a portion, or the entirety, of the interior surface of the one or more projections 130. The body of the shaft 126 and threaded portion 128 define aperture 132, which extends from the proximal end 122 to the distal end of the threaded portion 128 between the proximal end 122 and the distal end 124 of first portion 120. The aperture 132 provides access through the length of the first portion 120.

The second portion 140 comprises a proximal end 142, distal end 144, and a shaft 146 that defines a recess 148 and an aperture 152. The shaft 146 extends from the proximal end 142 to the distal end 144 of the second portion 140. The recess 148 extends from the proximal end 142 into the body of the shaft 146 towards the distal end 144 to base 145. The wall of the recess 148 defines threaded portion 150 that extends from the proximal end 142 towards the distal end 144 of the second portion 140. The recess 148 has a tapered configuration from its proximal end to its distal end at base 145 and is adapted to receive the threaded portion 128 and the one or more projections 130 of the first portion 120. The body of the shaft 146 defines aperture 152 that extends from the base 145 of the recess 148 to the distal end 142 of the second portion 140.

The control handle 100 can be formed of any suitable material and using any suitable method of manufacture. Example materials considered suitable include, but are not limited to, metals, plastics, or variations thereof, biocompatible materials, materials that can be made biocompatible, and any other material considered suitable for a particular application. In addition, while the first portion 120 has been described as having threaded portion 128 and the second portion 140 has been described as having threaded portion 150, other methods of providing releasable attachment between the two components are considered suitable, and skilled artisans will be able to select an appropriate type of attachment based on various considerations, such as the outside diameter of the probe, or other device, being utilized. Example methods of attachment considered suitable between the first portion and the second portion include, but are not limited to, providing a snap fit, pin vice, and/or a Morse taper.

While control handle 100 has been illustrated as having a particular external structural arrangement, a control handle can have any suitable external structural arrangement, and skilled artisans will be able to select a suitable external structural arrangement for a control handle according to a particular embodiment based on various considerations, including the structural arrangement of the device upon which the control handle is intended to be used. Example external structural arrangements considered suitable include, but are not limited to, linear, round, elliptical, oblong, tapered first portion and/or second portion, and any other structural arrangement considered suitable for a particular application.

FIG. 2 illustrates the exemplary detachable control handle 100 disposed on a probe 200 comprising a proximal end 201, a distal end 202, and a length that extends between the proximal end 201 and the distal end 202. In use, subsequent to the probe 200 being attached to a firing handle 220 of the lithotripter using cap 221, the control handle 100 is disposed along the length of the probe 200 by inserting the distal end 202 of the probe 200 through the aperture 132 of the first portion 120 and the aperture 152 of the second portion 140. Alternatively, control handle 100 can be disposed along the length of the probe 200 by inserting the distal end 202 of the probe 200 through the aperture 152 of the second portion 140 and the aperture 132 of the first portion 120.

In the first configuration, as illustrated in FIG. 1, the threaded portion 128 of the first portion 120 is free of the threaded portion 150 of the second portion 140 and the control handle 100 is slidably disposed along the length of the probe 200. In addition, in the first configuration, the first portion 120 along the length, or a portion of the length, of the one or more projections 130 is in a first state and has a first inside diameter. The first inside diameter in the first state is greater than, or slightly greater than, the outside diameter of the probe 200, allowing for the first portion 120 to be moveable along the length of the probe 200.

In the second configuration, as illustrated in FIG. 2, the threaded portion 128 of the first portion 120 is engaged with the threaded portion 150 of the second portion 140 such that the one or more projections 130 (e.g., collet configuration) are disposed within the recess 148 of the second portion 140. In the second configuration, the tapered configuration of the recess 148 compresses the distal end, a portion, or the entirety, of the one or more projections 130 against a portion of the exterior surface of the probe 200 to engage and/or lock the control handle 100 in place along the length of the probe 200. In addition, in the second configuration, the first portion 120 along the length, or a portion of the length, of the one or more projections 130 is in a second state and has a second inside diameter. The second inside diameter in the second state is equal to, or substantially equal to, the outside diameter of the probe 200, or is less than the inside diameter in the first state, allowing for the one or more projections 130 to engage and/or lock the control handle 100 in place along the length of the probe 200. Thus, in the second configuration the control handle 100 is releasably attached to the probe 200.

The configuration of the control handle 100 advantageously allows for removing the control handle 100 from the probe 200 and/or adjusting the position of the control handle 100 along the length of the probe 200. To accomplish adjusting the position of the control handle 100 along the length of the probe 200, a user moves the control handle 100 from the second configuration to the first configuration, or a position between the second configuration and the first configuration, and slides the control handle 100 to a desired position along the length of the probe 200. Then the user moves the control handle 100 back to the second configuration. To accomplish removing the control handle 100 from the probe 200 the user moves the control handle 100 from the second configuration to the first configuration, or a position between the second configuration and the first configuration, and slides the control handle 100 off of the probe 200.

The probe 200 optionally comprises one or more indicia (e.g., markers) disposed along its length. Each of the one or more indicia correlates with a length of probe that extends distal and/or proximal to the one or more indicia. For example, any form of measurement can be utilized to indicate to a user a length of probe disposed distal to the one or more indicia. In use, the one or more indicia assist a user in determining the length of the probe 200 disposed within a bodily passage.

The one or more indicia can be embedded within, and/or disposed on the interior or exterior surface of the probe 200. Alternatively, each of the one or more indicia can comprise a raised protuberance extending radially outward from the exterior surface of the probe 200. The raised protuberance can extend about the entirety of the circumference, or a portion of the circumference, of the probe 200. The inclusion of a raised protuberance is considered advantageous at least because it provides a user with tactile feedback as to the disposition of the control handle 100 along the length of the probe 200 as it is being releasably attached to the probe 200, allowing a user to releasably attached the control handle 100 at a particular location on the probe 200. For example, the control handle 100 can optionally comprise one or more recesses that circumferentially extend around the entirety, or a portion, of the interior surface of the first portion 120 and/or second portion 140 and are adapted to receive the one or more raised protuberances and position the control handle 100 at a particular location along the length of the probe 200.

The probe 200 can also optionally comprise a roughened surface along the entirety, or a portion, of the length of the probe 200. The inclusion of a roughened surface along the entirety, or a portion, of the length of the probe 200 is considered advantageous at least because it decreases the likelihood of the control handle 100 sliding from its position during use. The roughened surface can be accomplished in any suitable manner. Example methods considered suitable for producing a roughened surface along the entirety, or a portion, of the length of the probe 200 include, but are not limited to, grit blasting, sanding, and/or etching.

The probe 200 can be attached to any suitable device for performing treatment within a bodily passage. For example, to remove a stone disposed within a bodily passage, the probe 200 can be attached to a medical device such as a pneumatic lithotripter, ultrasonic lithotripter, and/or drill. Alternatively, control handle 100 can be attached to a laser fiber that is attached to a medical device such as a laser lithotripter. While particular medical devices have been described, the probe 200 and/or control handle 100 can be attached to any suitable medical device, and skilled artisans will be able to select an appropriate medical device according to a particular embodiment based on various considerations, such as the type of procedure being performed. Example medical devices considered suitable to include a control handle include, but are not limited to, probes, lithotripsy probes, optics, fiber optics, fibers, laser fibers, suction devices, irrigation devices, baskets, stone baskets, graspers, forceps, grasping forceps, drills, balloons, balloon catheters, and any other device considered suitable for a particular application (e.g., to treat a salivary duct).

Figure 3A:
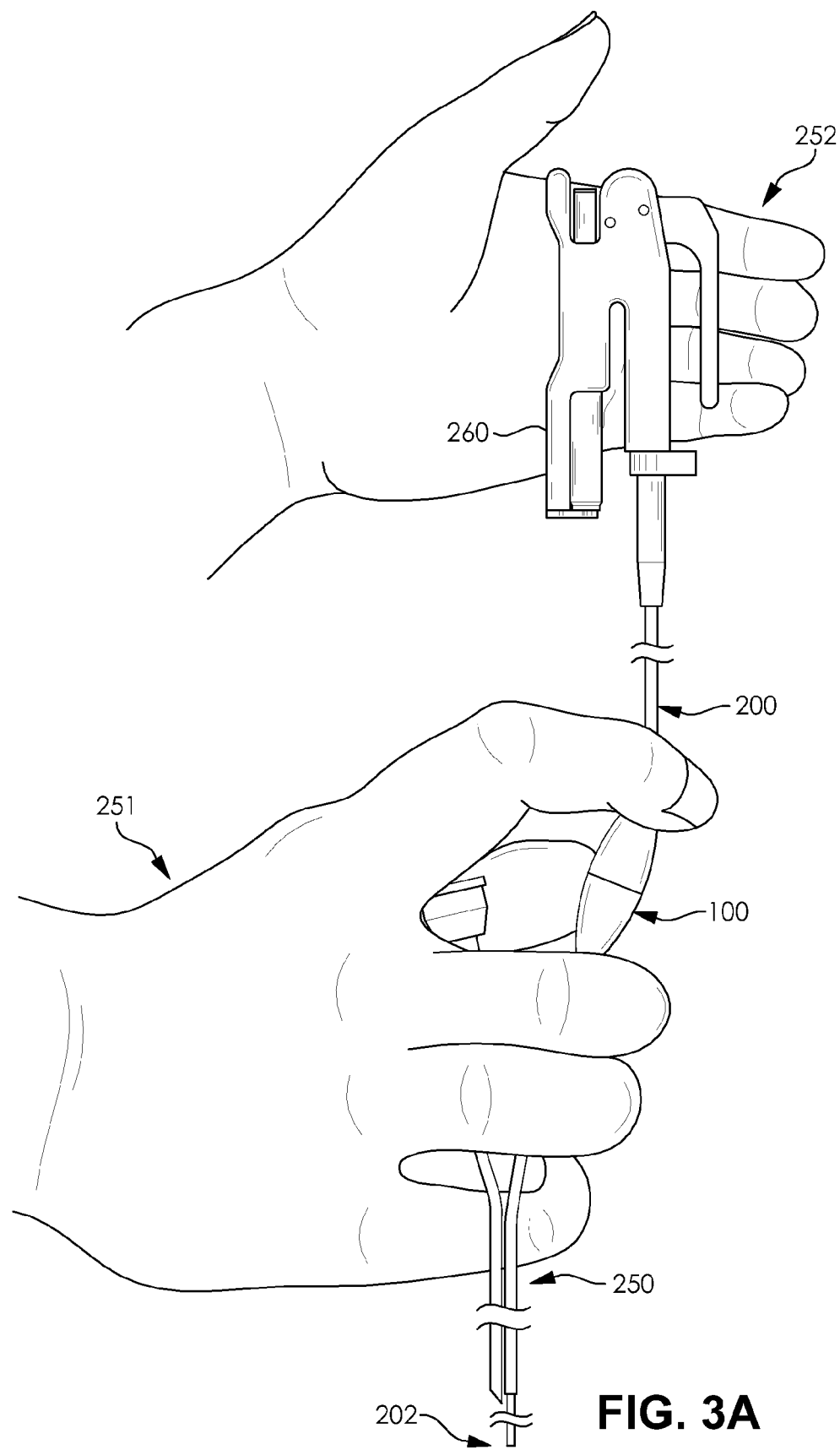
FIG. 3A is another side view of an exemplary control handle disposed on a probe that has been advanced through a scope.

In use, the control handle 100 advantageously provides a user with fine motor control of the probe 200 and tactile feedback relating to the treatment area and/or bodily passage. FIG. 3 illustrates fine motor control over the probe 200 using the detachable control handle 100. In FIG. 3 the probe 200 has been advanced through scope 250. FIG. 3A illustrates the fine motor control the right hand 251 of the user has over the probe 200 using the detachable control handle 100 and the gross motor control the left hand 252 has over the firing handle 260. Fine motor control is considered advantageous at least because it allows a user to properly position the distal end 204 of the probe 200 prior to activating the firing handle 260. For example, when a stone is being removed from a salivary duct, the control handle 100 provides a user with the ability to finely control the advancement of the probe 200 and provides tactile feedback as to when the probe 200 is in contact with a stone. Tactile feedback is considered advantageous at least because it allows a user to confirm proper placement of the probe 200 prior to activating the firing handle 260 of the lithotripter.

FIG. 4 illustrates the exemplary control handle 100 illustrated in FIG. 1 disposed on a probe 200 that has been advanced through a sheath 300 disposed in the opening of a salivary duct 320. In the illustrated embodiment, in addition to providing adjustability along the length of the probe 200 and tactile feedback, the control handle 100 also provides a user with the ability to control the length of the probe 200 that is passed into a bodily passage, such as a salivary duct. For example, FIG. 4 illustrates a sheath 300 disposed in the opening of a bodily passage to allow for the passage of treatment devices into the bodily passage. The sheath 300 comprises a proximal end 302, a distal end 304, and defines a lumen 306 that extends between an opening at the proximal end 302 and an opening at the distal end 304. In this example the bodily passage is a salivary duct 320, however it is considered suitable to utilize the control handles and/or probe configurations described herein in any bodily passage. The salivary duct 320 has a stone 340 disposed in its length. As the distal end 202 of the probe 200 is passed through the lumen 306 of the sheath, the distal end 104 of the control handle 100 acts as a mechanical stop by interacting with the proximal end 302 of the sheath, preventing advancement of the probe 200 beyond the position of the control handle 100. Thus, only the length of the probe 200 located distal to the control handle 100 is disposed through the lumen 306 of the sheath 300 and in the salivary duct 320. This advantageously prevents inadvertent advancement of the probe during the performance of a procedure. Optionally, sheath 300 can be omitted and control handle 100 can interact with the wall of the bodily passage.

FIG. 5 illustrates a side view of the exemplary control handle 100 illustrated in FIG. 1 disposed on a probe 200 that has been advanced through a scope 400. The scope 400 comprises a proximal end 402, a distal end 404, and defines a lumen (e.g., working channel) extending between an opening at the proximal end 402 and an opening at the distal end 404. The scope 400 can optionally comprise multiple lumens extending through the length of the scope. As illustrated in FIG. 5, the distal end 202 of the probe 200 has been inserted through the proximal end and lumen of the scope 400 and the distal end 104 of the control handle 100 is acting as a mechanical stop by preventing advancement of the probe 200 beyond the position of the control handle 100. Thus, only the length of the probe 200 located distal to the control handle 100 is disposed through the lumen of the scope 400, leaving the scope 400 disposed between the distal end 202 of the probe 200 and the distal end 104 of the control handle 100.

Figure 6:
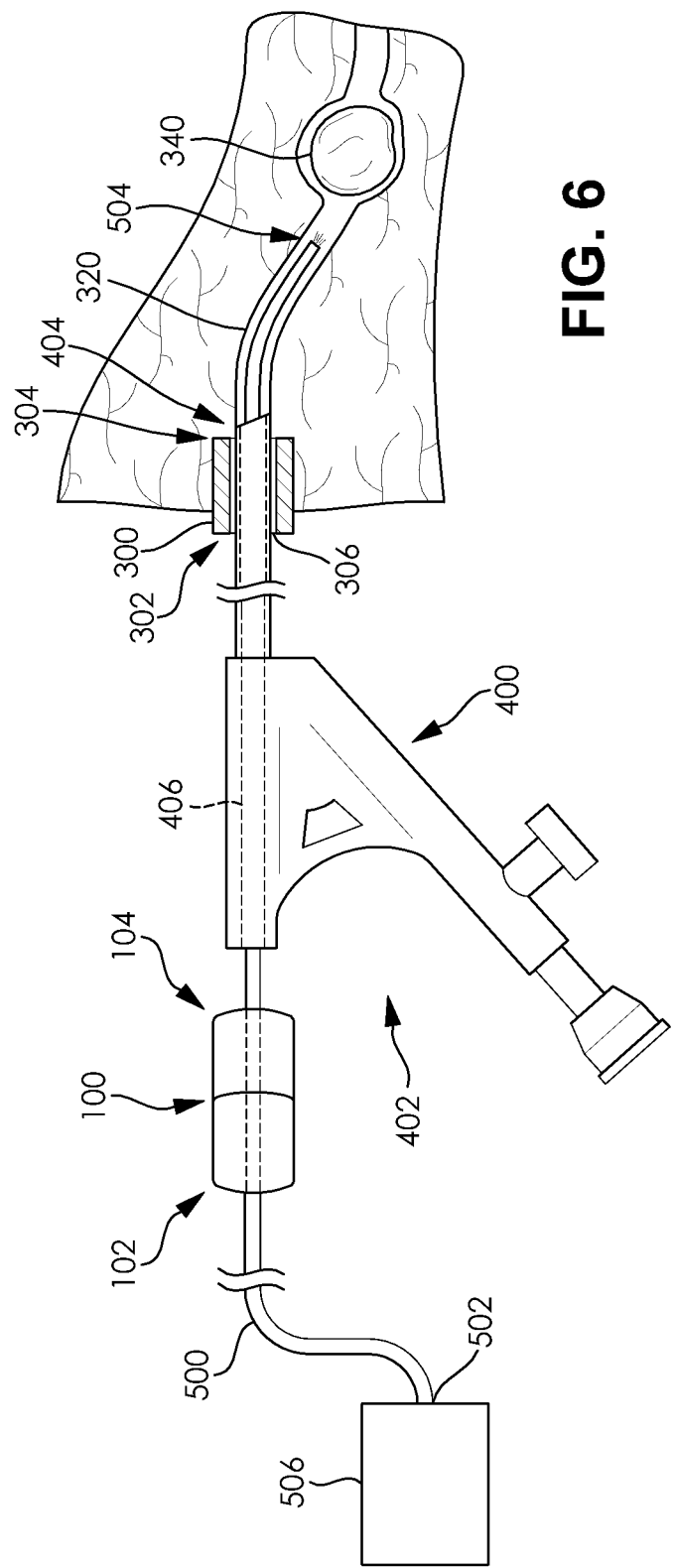
FIG. 6 is a side view of the exemplary control handle illustrated in FIG. 1 disposed on a laser fiber that has been advanced through a scope and a sheath disposed in the opening of a salivary duct.

FIG. 6 illustrates a side view of the exemplary control handle 100 illustrated in FIG. 1 disposed on a laser fiber 500 that has been advanced through a scope 400 and a sheath 300 disposed in the opening of a salivary duct 320. The sheath 300 is similar to sheath 300 illustrated in FIG. 4, and described above, except as detailed below. The scope 400 is similar to scope 400 illustrated in FIG. 5, and described above, except as detailed below. Reference numbers in FIG. 6 refer to the same structural element or feature referenced by the same number in FIGS. 4 and 5. Thus, sheath 300 has a proximal end 302, a distal end 304, and defines a lumen 306 and scope 400 has a proximal end 402, a distal end 404, and defines a lumen 406 that extends from an opening on the proximal end 402 to an opening on the distal end 404.

In the illustrated embodiment, sheath 300 is disposed in the opening of a salivary duct 320 and the distal end 404 of scope 400 has been advanced through the lumen 306 defined by the sheath 300 and towards a point of treatment (e.g., stone 340). Control handle 100 is disposed along the length of a laser fiber 500 that has a proximal end 502 and a distal end 504. The proximal end 502 of the laser fiber 500 is operatively attached to an energy source 506 that is adapted to transmit energy along the length of the laser fiber 500. The control handle 100 is disposed between the proximal end 502 and the distal end 504 of the laser fiber 500 such that when the distal end 504 of the laser fiber 500 has been inserted through lumen 406 defined by scope 400 the distal end 104 of the control handle 100 acts as a mechanical stop by preventing advancement of the laser fiber 500 through the scope 400 beyond the position of the control handle 100. Thus, only the length of the laser fiber 500 located distal to the control handle 100 can be advanced through lumen 406 define by the scope 400, sheath 300, and salivary duct 320. Optionally, sheath 300 can be omitted and scope 400 can independently be advanced through the opening of a bodily passage.

Any suitable laser fiber 500 and/or energy source 506 can be used in combination with control handle 100, and skilled artisans will be able to select a suitable laser fiber and/or energy source according to a particular embodiment based on various considerations, including the type of procedure intended to be completed.

FIG. 7 illustrates a second exemplary control handle 600. Control handle 600 is similar to control handle 100 illustrated in FIG. 1, and described above, except as detailed below. Reference numbers in FIG. 7 refer to the same structural element or feature referenced by the same number in FIG. 1, offset by 500. Thus, control handle 600 comprises a proximal end 602, a distal end 604, a first portion 620, and a second portion 640 and has a first configuration and a second configuration. FIG. 7 illustrates control handle 600 in the first configuration.

In the illustrated embodiment, alternative to including one or more projections (e.g., projections 130 illustrated in FIG. 1), the wall of the first portion 620 defines threaded portion 628 between the proximal end 622 and distal end 624, projection 630, and a recess 670 that extends into the body of projection 630 from the distal end 624 and towards the proximal end 622 to a recess base 672. Alternatively, projection 630 can be omitted and recess 670 can extend into threaded portion 628.

In the illustrated embodiment, control handle 600 includes a compressible member 680 and a rigid member 690. Compressible member 680 has a proximal end 682, a distal end 684, and defines a lumen 686 that extends from an opening on the proximal end 682 to an opening on the distal end 684. Rigid member 690 has a proximal end 692, a distal end 694, and defines a lumen 696 that extends from an opening on the proximal end 692 to an opening on the distal end 694. Compressible member 680 can comprise any suitable compressibility and rigid member 690 can comprise any suitable rigidity. Compressible member 680 need only be compressible relative to rigid member 690.

Compressible member 680 and rigid member 690 can be formed of any suitable material, and skilled artisans will be able to select a suitable material for a compressible member and/or a rigid member according to a particular embodiment based on various considerations, including the material forming a control handle. Example materials considered suitable to form a compressible member include, but are not limited to, biocompatible materials, materials that can be made biocompatible, polymers, flexible polymers, materials that are deformable, and any other material considered suitable for a particular application. Example materials considered suitable to form a rigid member include, but are not limited to, biocompatible materials, materials that can be made biocompatible, polymers, rigid polymers, metals, and any other material considered suitable for a particular application.

Compressible member 680 is disposed within recess 670 such that the proximal end 682 of compressible member 680 is disposed adjacent recess base 672. Rigid member 690 is disposed within recess 670 such that the proximal end 692 of rigid member 690 is disposed adjacent the distal end 684 of compressible member 680 and the distal end 694 of the rigid member 690 is disposed adjacent the recess base 645 of the second portion 640. When control handle 600 is moved to its second configuration, in which first portion 620 and second portion 640 are releasably attached to one another, the distal end 694 of rigid member 690 contacts recess base 645 of second portion 640 and the proximal end 692 of rigid member 690 compresses against the distal end 684 of compressible member 680. As first portion 620 is threaded onto second portion 640, or vice versa, rigid member 690 is compressed against compressible member 680 such that compressible member 680 deforms and the lumen 686 defined by compressible member 680 is reduced in diameter such that it grips any device passing through lumen 632 and/or lumen 652. Thus, when control handle 600 is in the first configuration lumen 686 defines a first inner diameter and when control handle 600 is in the second configuration lumen 686 defines a second inner diameter that is less than the first inner diameter.

While compressible member 680 and rigid member 690 have been illustrated and described as being disposed within recess 670 such that the proximal end 682 of compressible member 680 is disposed adjacent recess base 672 and the proximal end 692 of rigid member 690 is disposed adjacent the distal end 684 of compressible member 680, any suitable configuration is considered suitable. For example, alternative to the above configuration, rigid member 690 can be disposed within recess 670 such that the proximal end 692 of rigid member 690 is disposed adjacent recess base 672 and compressible member can be disposed within recess 670 such that the proximal end 682 of compressible member 680 is disposed adjacent the distal end 694 of rigid member 690. Thus, a portion of compressible member 680 and/or rigid member 690 can be disposed within one or the recess 670 defined by the first portion 620 or the recess 648 defined by the second portion 640.

While a compressible member 680 and rigid member 690 have been illustrated and described as providing a mechanism for releasably attaching control handle 600 to a device (e.g., probes, lithotripsy probes, optics, fiber optics, fibers, laser fibers, suction devices, irrigation devices, baskets, stone baskets, graspers, forceps, grasping forceps, drills, balloons, balloon catheters), releasable attachment between a control handle and a device can be accomplished using any suitable number of compressible members and/or rigid members. Skilled artisans will be able to select a suitable number of compressible members and/or rigid members to include in a control handle according to a particular embodiment based on various considerations, including the type of device the control handle is being releasably attached. For example, compressible member and rigid member can be integrated components such that a first portion of a member is compressible with respect to a second portion of the member. Alternatively, a compressible member can be utilized independent of a rigid member.

FIG. 8 illustrates a third exemplary control handle 700 comprising a body 702 and a fastener 704. Body 702 comprises a proximal end 706, a distal end 708, and defines a first lumen 710 and a second lumen 712. First lumen 710 extends from a first opening 714 defined on the proximal end 706 to a second opening 716 defined on the distal end 708. Second lumen 712 extends from a first opening 718 defined between the proximal end 706 and the distal end 708 to a second opening 720 defined along the length of first lumen 710. Second lumen 712 is in communication with first lumen 710. Second lumen 712 is threaded along its length, or a portion thereof, and is adapted to receive a portion of fastener 704. Fastener 704 has a first end 730 and a second end 732 and is threaded from the second end 732 towards the first end 730.

Control handle 700 has a first configuration and a second configuration. In the first configuration, fastener 704 is disposed between opening 718 and opening 720 and in the second configuration fastener 704 is disposed within opening 720 and/or within lumen 710. In use, a device (e.g., probe 200, laser fiber 500) is passed through the first lumen 710 such that the control handle 700 is disposed between the proximal end of the device and the distal end of the device. Fastener 704 is then advanced through second lumen 712 towards first lumen 710 until it contacts and compresses against the device attaching control handle 700 to the device.

Control handle 700 can be formed of any suitable material using any suitable method of manufacture, and skilled artisans will be able to select a suitable material and method of manufacture according to a particular embodiment based on various considerations, including the material forming the device on which the control handle is intended to be used. Example materials considered suitable include, but are not limited to, biocompatible materials, materials that can be made biocompatible, metals, polymers, flexible materials, and any other material considered suitable for a particular application.

FIGS. 9 and 10 illustrate a fourth exemplary control handle 800 comprising a first portion 802 and a second portion 804. Control handle 800 has a first configuration, as illustrated in FIG. 9, and a second configuration, as illustrated in FIG. 10.

First portion 802 has a proximal end 806, a distal end 808, and a body 810 that has a first side 812 and defines a recess 814 and a protuberance 816. First side 812 extends from the proximal end 806 to the distal end 808 of first portion 802 and is complementary to second side 826 of second portion 804. Recess 812 extends from the proximal end 806 to the distal end 808 of first portion 802 and into body 810 from first side 812. Protuberance 816 extends radially outward from first side 812 and has a lip 818 that extends towards recess 812.

Second portion 804 has a proximal end 820, a distal end 822, and a body 824 that has a second side 826 and defines a first recess 828 and a second recess 830. Second side 826 extends from the proximal end 820 to the distal end 822 of second portion 804 and is complementary to first side 812 of first portion 802. First recess 828 extends from the proximal end 820 to the distal end 822 of second portion 804 and into body 824 from second side 826. Second recess 830 extends into body 824 between the proximal end 820 and distal end 822 of second portion 804 and is adapted to receive a portion or the entirety of lip 818.

Hinges 832 hingedly connect first portion 802 and second portion 804 to one another. Any suitable number of hinges and/or type of hinge can be used to hingedly connect a first portion to a second portion, and skilled artisans will be able to select a suitable number of hinges and/or type of hinge according to a particular embodiment based on various considerations, including the material forming the first portion and second portion. Example number of hinges considered suitable include, but are not limited to, at least one, one, two, a plurality, three, four, and any other number considered suitable for a particular application. Example type of hinges considered suitable include, but are not limited to, hinges formed integrally with the first portion and the second portion, and any other type of hinge considered suitable for a particular application.

First portion 802 and second portion 804 can be formed of any suitable material and using any suitable method of manufacture, and skilled artisans will be able to select a suitable material and method of manufacture according to a particular embodiment based on various considerations, including the material forming the device on which a control handle is intended to be used. Example materials considered suitable include, but are not limited to, metals, polymers, flexible materials, biocompatible materials, materials that can be made biocompatible, and any other material considered suitable for a particular application.

In use, a device (e.g., probe 200, laser fiber 500) is placed between the first portion 802 and second portion 804 when control handle 800 is in the first configuration such that the control handle 800 is disposed between the proximal end of the device and the distal end of the device. Control handle 800 is then moved to its second configuration such that it compresses against the device attaching control handle 800 to the device.

Figure 11:
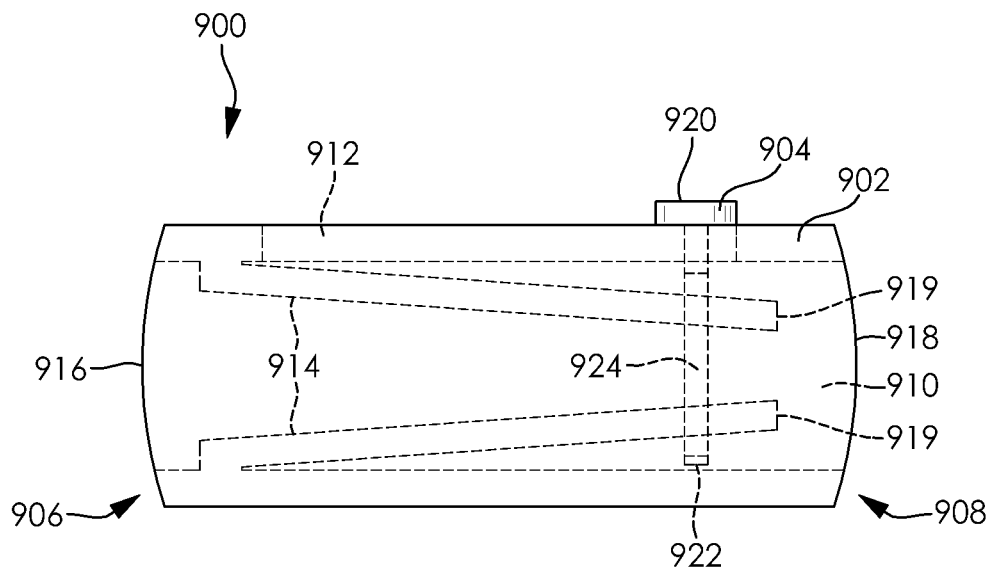
FIG. 11 is a side view of a fifth exemplary control handle in a first configuration.
Figure 12:
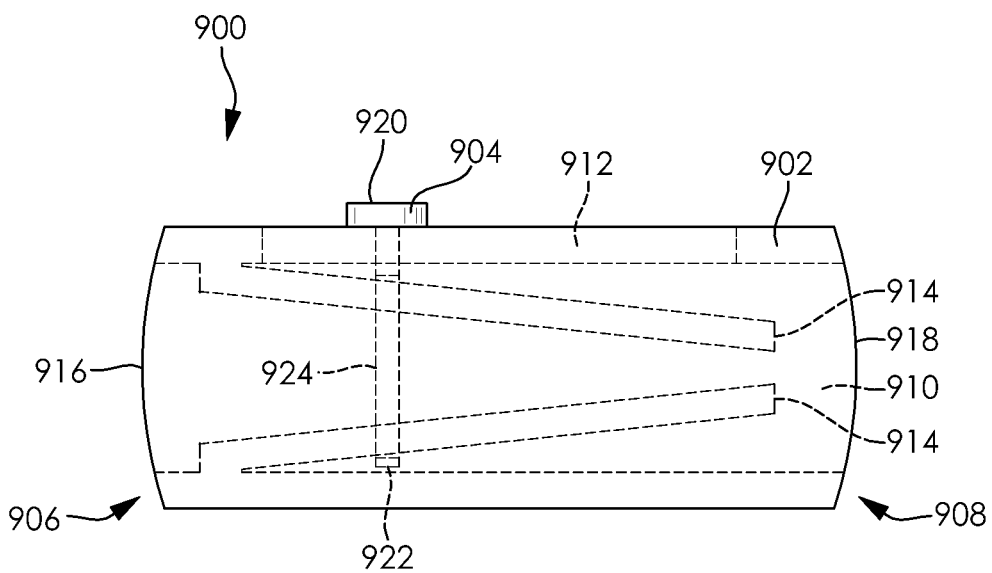
FIG. 12 is a side view of the fifth exemplary control handle in a second configuration.

FIGS. 11 and 12 illustrate a fifth exemplary control handle 900 comprising a body 902 and an actuator 904. Control handle 900 has a first configuration, as illustrated in FIG. 11, and a second configuration, as illustrated in FIG. 12.

Body 902 has a proximal end 906, a distal end 908, and defines a lumen 910, an opening 912, and a plurality of arms 914. Lumen 910 extends from a first opening 916 on the proximal end 906 to second opening 918 on the distal end 908. Opening 912 is disposed between the proximal end 906 and the distal end 908, extends through the body 902, and is in communication with lumen 910. Each arm of the plurality of arms 914 extends from body 902 into lumen 910 and towards the distal end 908 of body 902 to an arm distal end 919. Each arm of the plurality of arms 914 is pivotably connected to body 902 such that it can move from a first position to a second position.

Actuator 904 has a first end 920 and a second end 922 and is slidable along the length of body 902. First end 920 is disposed on the exterior surface of body 902 and the second end 922 is disposed within lumen 910. The body of actuator 904 defines an aperture 924 between the first end 920 and second end 922 of actuator 904 that is disposed within lumen 910 and is adapted to receive each arm of the plurality of arms 914 and a device on which control handle 900 is intended to be releasably attached. Actuator 904 has a first configuration, as shown in FIG. 11, and a second configuration, as shown in FIG. 12. Movement of actuator 902 from the first configuration to the second configuration moves each arm of the plurality of arms 914 from its first position to its second position. When actuator 902 is in the first configuration a first distance is defined between a first arm of the plurality of arms 914 and a second arm of the plurality of arms 914. When actuator 902 is in the second configuration a second distance, less than the first distance, is defined between the first arm of the plurality of arms 914 and the second arm of the plurality of arms 914.

Control handle 900 can be formed of any suitable material and using any suitable method of manufacture, and skilled artisans will be able to select a suitable material and method of manufacture according to a particular embodiment based on various considerations, including the material forming the device on which a control handle is intended to be used. Example materials considered suitable include, but are not limited to, metals, polymers, flexible materials, biocompatible materials, materials that can be made biocompatible, and any other material considered suitable for a particular application.

In use, a device (e.g., probe 200, laser fiber 500) is placed within lumen 910 when actuator is in the first configuration and each arm of the plurality of arms 914 is in the first position such that the control handle 900 is disposed between the proximal end of the device and the distal end of the device. Actuator 900 is then moved to its second configuration such that it moves each arm of the plurality of arms 914 to its second position attaching control handle 900 to the device.

While a plurality of arms 914 have been illustrated and described, any suitable number of arms can be included in a control handle. Skilled artisans will be able to select a suitable number of arms to include in a control handle according to a particular embodiment based on various considerations, including the device on which the control handle is intended to be releasably attached. Example number of arms considered suitable to include in a control handle include, but are not limited to, at least one, one, two, a plurality, three, four, and any other number considered suitable for a particular embodiment.

While particular configurations for the control handle (e.g., control handle 100, control handle 600, control handle 700, control handle 800, control handle 900) have been illustrated and described, other configurations are considered suitable, and skilled artisans will be able to select an appropriate configuration for a control handle according to a particular embodiment based on various considerations, such as the outside diameter of the device (e.g., probe, laser fiber) upon which the control handle is intended to be used. Examples of alternative control handle configurations considered suitable include, but are not limited to, pin clamps, locking torque device, tubular members, and/or tubular members that comprise a setscrew.

Various methods, steps, optional steps, and alternative steps of performing a method of treatment are provided. While the methods, steps, optional steps, and alternative steps described herein are shown and described as a series of acts, it is to be understood and appreciated that the methods, steps, optional steps, and alternative steps are not limited by the order of acts, as some acts may, in accordance with these methods, occur in different orders, be omitted, and/or occur concurrently with other acts described herein.

Figure 13:
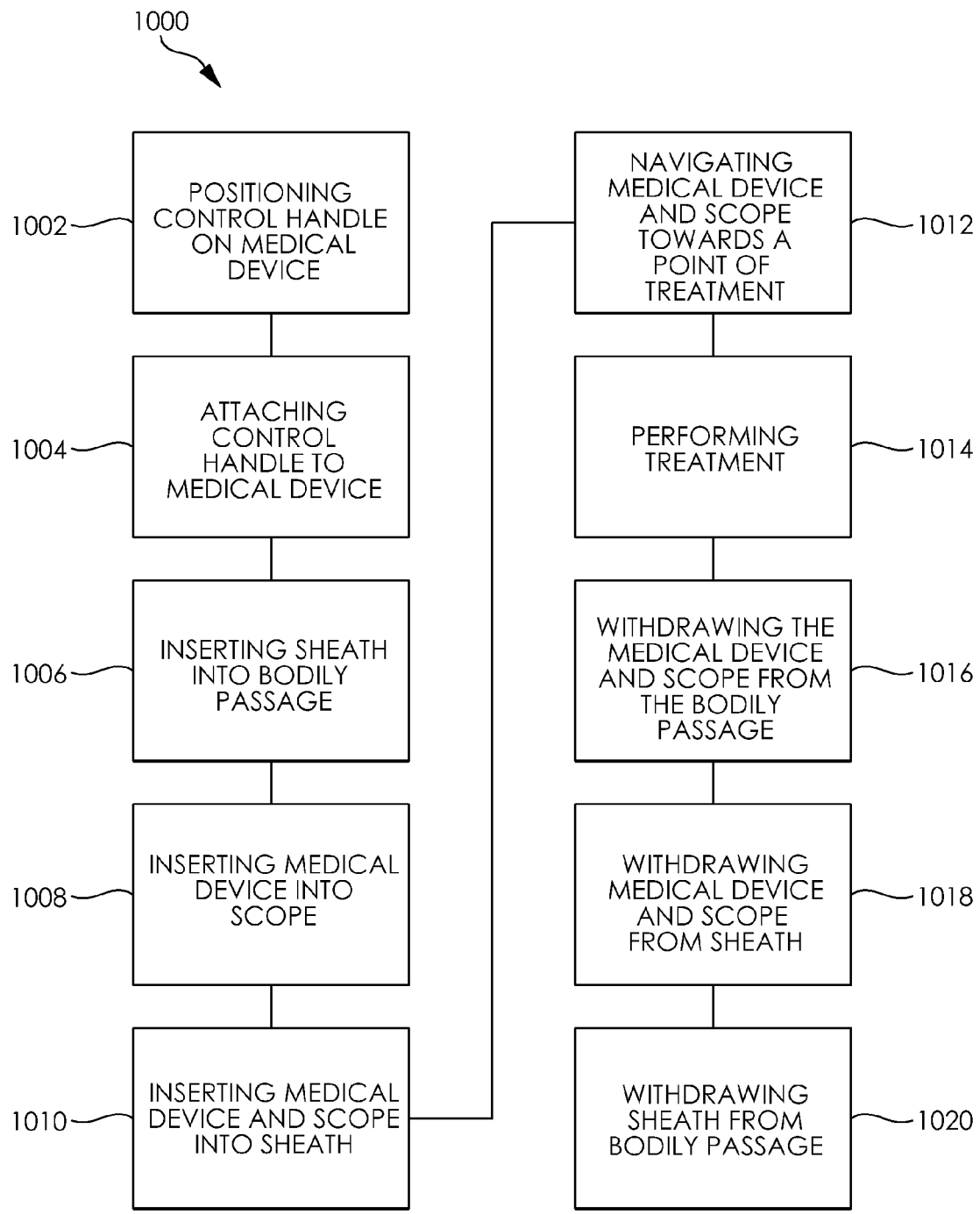
FIG. 13 is a flowchart representation of an exemplary method of treatment.

FIG. 13 is a flowchart representation of an exemplary method 1000 of treatment. A step 1002 comprises positioning a control handle on a medical device at a predetermined location. The medical device comprising a proximal end and a distal end. Another step 1004 comprises releasably attaching the control handle to the medical device. Another step 1006 comprises inserting a sheath having a proximal end and a distal end through an opening in a bodily passage such that the distal end of the sheath is disposed past the opening and in the bodily passage. The sheath defines a lumen that extends between an opening at the proximal end and an opening at the distal end of the sheath. Another step 1008 comprises inserting the distal end of the medical device into a lumen defined by a scope having a proximal end and a distal end such that the distal end of the medical device is disposed distal to the distal end of the scope. The lumen of the scope extends between an opening at, or near, the proximal end of the scope and an opening at the distal end of the scope. Another step 1010 comprises inserting the distal end of the medical device and the distal end of the scope through the lumen defined by the sheath such that the distal end of the medical device and the distal end of the scope are disposed distal to the distal end of the sheath. Another step 1012 comprises navigating the distal end of the medical device and the distal end of the scope through the bodily passage and towards a point of treatment. Another step 1014 comprises preforming treatment using the medical device. Another step 1016 comprises withdrawing the medical device and the scope from the bodily passage. Another step 1018 comprises withdrawing the medical device and the scope from the lumen defined by the sheath. Another step 1020 comprises withdrawing the sheath from the opening of the bodily passage.

The step 1002 of positioning a control handle on a medical device at a predetermined location can be accomplished based upon various measured and/or physiological factors, and skilled artisans will be able to select a suitable measurement and/or physiological factor to base the positioning of a control handle on a medical device according to a particular embodiment based on various considerations, including the treatment intended to be performed. Example measurements and/or physiological factors considered suitable to base the positioning of a control handle on a medical device include, but are not limited to, the structural arrangement of a bodily passage, an estimate as to the length of the medical device desired to be introduced into a bodily passage, the location of a point of treatment within a bodily passage, a previously determined measurement (e.g., the location of a stone within a bodily passage), and any other measurement and/or physiological factor considered suitable for a particular application. Alternatively, a control handle can be positioned on a medical device at any suitable location between the proximal end and the distal end of the medical device.

It is considered advantageous to position a control handle on a medical device at least because it provides a mechanism for providing fine motor control over the medical device and it provides a mechanical stop to the distal advancement of the medical device within the bodily passage. For example, if the medical device is advanced through a sheath or scope, the distal end of the control handle will interact with the proximal end of the sheath or scope to prevent the medical device from advancing within a bodily passage beyond the location of the control handle.

A control handle can be positioned on any suitable medical device, and skilled artisans will be able to select a suitable medical device according to a particular embodiment based on various considerations, including the procedure intended to be performed. Example medical devices considered suitable include, but are not limited to, probes, lithotripsy probes, optics, fiber optics, fibers, laser fibers, suction devices, irrigation devices, baskets, stone baskets, graspers, forceps, grasping forceps, drills, balloons, balloon catheters, and any other device considered suitable for a particular application (e.g., to treat a salivary duct).

An optional step comprises measuring the bodily passage and/or determining the distance to a point of treatment within the bodily passage. This step can be accomplished using any suitable method, and skilled artisans will be able to select a suitable method according to a particular embodiment based on various considerations, including the location of the bodily passage. Example methods of measuring a bodily passage and/or determining the distance to a point of treatment within the bodily passage include, but are not limited to, using x-ray technology, and any other method considered suitable for a particular application.

The step 1004 of attaching a control handle to the medical device can be accomplished using any of the control handles illustrated and/or described herein and by moving the control handle from a first configuration to a second configuration, or a configuration between the first configuration and the second configuration. Example control handles considered suitable include, but are not limited to, control handle 100, control handle 600, control handle 700, control handle 800, control handle 900, and any other control handle considered suitable for a particular application.

The step 1006 of inserting a sheath having a proximal end and a distal end through an opening in a bodily passage such that the distal end of the sheath is disposed past the opening and in the bodily passage can be accomplished by locating an opening of a bodily passage (e.g., salivary duct opening), or creating an opening into a bodily passage, and inserting the distal end of the sheath into and through the opening of the bodily passage. The sheath defines a lumen that extends between an opening at the proximal end and an opening at the distal end (e.g., sheath 300).

Step 1006 can be accomplished using any suitable sheath, formed of any suitable material, having any suitable length, and defining at least one lumen. Skilled artisans will be able to select a suitable sheath to insert into a bodily passage according a particular embodiment based on various considerations, including the bodily passage within which the sheath is intended to be deployed. Optionally, step 1006 can be omitted and the medical device and/or scope can be independently inserted through an opening in a bodily passage such that the distal end of the medical device and/or scope is disposed past the opening and in the bodily passage.

While step 1006 has been described as using a sheath to provide access to a bodily passage, other devices are considered suitable, and skilled artisans will be able to select a suitable device according to a particular embodiment based on various considerations, such as the treatment intended to be performed. Example devices considered suitable include, but are not limited to, a scope defining at least one lumen, and any other device considered suitable for a particular application. Optionally, step 1006 can be omitted and a medical device and/or scope can be passed through an opening and into a bodily passage independent of a sheath such that the distal end of the medical device and/or scope is disposed within the bodily passage.

The step 1008 of inserting the distal end of the medical device into a lumen defined by a scope having a proximal end and a distal end such that the distal end of the medical device is disposed distal to the distal end of the scope can be accomplished by locating a lumen (e.g., working channel) of a scope and inserting the distal end of the medical device through the lumen of the scope. The lumen of the scope extends between an opening at, or near, the proximal end of the scope and an opening at the distal end of the scope. Step 1008 can be accomplished using any suitable scope, formed of any suitable material, having any suitable length, and defining at least one lumen. Skilled artisans will be able to select a suitable scope according to a particular embodiment based on various considerations, including the bodily passage within which a scope is intended to be deployed. Optionally, step 1008 can be omitted and a medical device can be passed through a sheath independent of a scope such that the distal end of the medical device is disposed within the bodily passage.

The step 1010 of inserting the distal end of the medical device and the distal end of the scope through the lumen defined by the sheath such that the distal end of the medical device and the distal end of the scope are disposed distal to the distal end of the sheath can be accomplished by locating the opening defined on the proximal end of the sheath and inserting the distal end of the medical device and the distal end of the scope into and through the opening of the sheath and advancing the medical device and the scope distally through the sheath. Alternatively, the medical device can be passed independently through the lumen of the sheath. Alternatively, the scope can be passed independently through the lumen of the sheath.

The step 1012 of navigating the distal end of the medical device and the distal end of the scope through the bodily passage and towards a point of treatment (e.g., a stone disposed within a salivary duct) can be accomplished by placing a distal force on any portion of the medical device and/or scope to provide axial movement of the distal end of the medical device and/or scope through the bodily passage. Alternatively, the distal end of the medical device can be navigated independent of the scope through the bodily passage and towards a point of treatment. Alternatively, the distal end of the scope can be navigated independent of the medical device through the bodily passage and towards a point of treatment.

The step 1014 of performing treatment using the medical device can be accomplished using any suitable method of treatment, and skilled artisans will be able to select a suitable method of treatment according to a particular embodiment based on various considerations, including the medical device being navigated through the bodily passage. Example methods of treatment considered suitable include, but are not limited to, performing lithotripsy (e.g., pneumatic lithotripsy, ultrasonic lithotripsy, laser lithotripsy), removing material from the bodily passage with a suction device, irrigating the bodily passage with an irrigation device, and any other method of treatment considered suitable for a particular application.

An optional step comprises contacting the distal end of the medical device (e.g., probe, laser fiber) with a stone disposed in the bodily passage. This step can be accomplished using direct visualization, with the aid of a scope, and/or through tactile feedback through the control handle. This step can be accomplished prior to, during, or subsequent to, step 1014 of performing treatment using the medical device.

Another optional step comprises adjusting the position of control handle along the length of the medical device. This step can be accomplished prior to, during, or subsequent to the step of measuring the bodily passage, the step of determining the distance to a point of treatment, and/or the step of contacting the distal end of the medical device with a stone disposed in the bodily passage.

The step 1016 of withdrawing the medical device and scope from the bodily passage can be accomplished by applying a proximal force on any suitable portion of the medical device and/or scope until the medical device and the scope are completely removed from the bodily passage. Alternatively, the medical device can be withdrawn from the bodily passage independent of the scope. Alternatively, the scope can be withdrawn from the bodily passage independent of the medical device.

The step 1018 of withdrawing the medical device and scope from the lumen defined by the sheath can be accomplished by applying a proximal force on any suitable portion of the medical device and/or scope until the medical device and scope are completely removed from the sheath. Alternatively, the medical device can be withdrawn from the sheath independent of the scope. Alternatively, the scope can be withdrawn from the sheath independent of the medical device.

The step 1020 of withdrawing the sheath from the opening of the bodily passage can be accomplished by applying a proximal force on any suitable portion of the sheath until the sheath is completely removed from the opening of the bodily passage. Optionally, the step of removing the medical device and/or scope from the lumen of the sheath can be accomplished in combination with the step of removing the sheath from the opening of the bodily passage.

An optional step comprises inserting the distal end of a second medical device into the lumen defined by the sheath or a lumen defined by the scope such that the distal end of the second medical device is disposed within the bodily passage. Any suitable medical device can be used to accomplish this step, and skilled artisans will be able to select a suitable medical device according to particular embodiment based on various considerations, including the treatment intended to be performed. Example medical devices considered suitable include, but are not limited to, lithotripsy devices (e.g., probes, laser fibers), suction devices, irrigation devices, graspers, forceps, grasping forceps, baskets, stone baskets, drills, balloons, balloon catheters, optics, fiber optics, fibers, and any other medical device considered suitable for a particular application (e.g., to treat a salivary duct).

Another optional step comprises navigating the second medical device towards a point of treatment. This step can be accomplished by placing a distal force on any portion of the medical device to provide axial movement of the distal end of the medical device through the bodily passage.

Another optional step comprises performing treatment using the second medical device. This step can be accomplished by activating the medical device or performing a method of treatment using the medical device.

Another optional step comprises withdrawing the second medical device from the bodily passage. This step can be accomplished by applying a proximal force on any suitable portion of the medical device until the medical device is completely removed from the bodily passage.

Another optional step comprises withdrawing the second medical device from the lumen defined by the sheath. This step can be accomplished by applying a proximal force on any suitable portion of the medical device until the medical device is completely removed from the sheath.

Another optional step comprises confirming the completion of the treatment (e.g., stone fragmentation, removal of the stone fragments from the salivary duct). This step can be accomplished using the scope, direct visualization, or any other suitable method and/or device.

While the various steps, alternative steps, and optional steps have been described above with respect to performing a method of treatment, these steps, alternative steps, and optional steps can be accomplished with respect to treating any suitable condition within any suitable bodily passage including, but not limited to, a salivary duct, the urinary tract, and any other bodily passage considered suitable for a particular application. In addition, these steps, alternative steps, and optional steps can be included in, accomplished concurrently with, and/or accomplished in the alternative to, the methodologies, steps, alternative steps, and/or optional steps described below with respect to the exemplary method 1100 of removing a stone disposed in a salivary duct.

Figure 14:
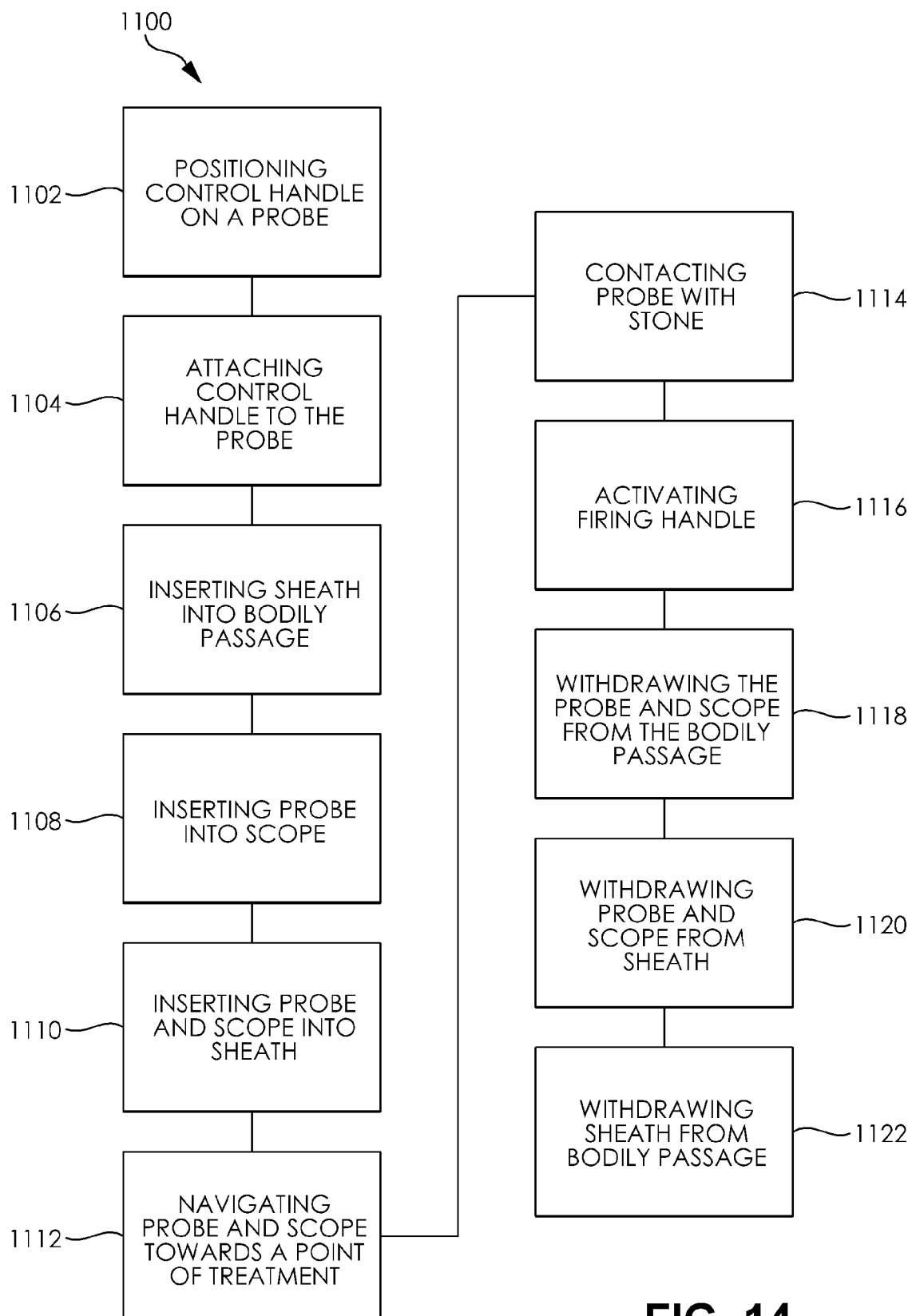
FIG. 14 is a flowchart representation of another exemplary method of treatment.

FIG. 14 is a flowchart representation of an exemplary method 1100 of removing a stone disposed in a salivary duct. A step 1102 comprises positioning a control handle on a probe at a predetermined location. The probe comprises a proximal end and a distal end and is attached to a lithotripter having a firing handle. Another step 1104 comprises releasably attaching the control handle to the probe. Another step 1106 comprises inserting a sheath having a proximal end and a distal end through a salivary duct opening such that the distal end of the sheath is disposed past the opening and in the salivary duct. The sheath defines a lumen that extends between an opening at the proximal end and an opening at the distal end of the sheath. Another step 1108 comprises inserting the distal end of the probe into a lumen defined by a scope having a proximal end and a distal end such that the distal end of the probe is disposed distal to the distal end of the scope. The lumen of the scope extends between an opening at, or near, the proximal end of the scope and an opening at the distal end of the scope. Another step 1110 comprises inserting the distal end of the probe and the distal end of the scope through the lumen defined by the sheath such that the distal end of the probe and the distal end of the scope are disposed distal to the distal end of the sheath. Another step 1112 comprises navigating the distal end of the probe and the distal end of the scope through the salivary duct and towards a point of treatment. Another step 1114 comprises contacting the distal end of the probe with a stone disposed in the salivary duct. Another step 1116 comprises activating the firing handle of the lithotripter to transmit energy through the probe and to the stone to fragment the stone. Another step 1118 comprises withdrawing the probe and the scope from the bodily passage. Another step 1120 comprises withdrawing the probe and the scope from the lumen defined by the sheath. Another step 1122 comprises withdrawing the sheath from the opening of the bodily passage.

While a probe has been described with respect to methodology 1100, any suitable medical device can be used to perform a method of treatment, such as lithotripsy. Skilled artisans will be able to select a suitable medical device according to a particular embodiment based on various considerations, including the type of treatment intended to be performed. Example medical devices considered suitable include, but are not limited to, probes, lithotripsy probes, optics, fiber optics, fibers, laser fibers, suction devices, irrigation devices, baskets, stone baskets, graspers, forceps, grasping forceps, drills, balloons, balloon catheters, and any other device considered suitable for a particular application (e.g., to treat a salivary duct). For example, alternative to using a probe, methodology 1100 can be accomplished using a laser fiber operatively connected to an energy source.

The step 1116 of activating the firing handle of the lithotripter to transmit energy through the probe and to the stone to fragment the stone can be accomplished by depressing the firing handle of the lithotripter. Alternatively, if laser lithotripsy is being performed, an energy source can be activated to fragment the stone.

An optional step comprises inserting an irrigation device having a proximal end and a distal end through the lumen of the sheath such that the distal end of the irrigation device is disposed distal to the distal end of the sheath. This step can be accomplished by locating the opening defined on the proximal end of the sheath and inserting the distal end of the irrigation device into and through the opening of the sheath. This step can be accomplished using any suitable irrigation device that is adapted to introduce any suitable fluid (e.g., water, saline) into a bodily passage to assist with the removal of material (e.g., stone fragments) from the bodily passage. Alternative to advancing an irrigation device, one or more other medical devices may be advanced through the lumen of the sheath and used to remove the stone, and/or stone fragments, disposed within the salivary duct, and skilled artisans will be able to select a suitable medical device based on various considerations, such as the location of the stone within the salivary duct. Example medical devices considered suitable include, but are not limited to, probes, lithotripsy probes, optics, fiber optics, fibers, laser fibers, suction devices, irrigation devices, baskets, stone baskets, graspers, forceps, grasping forceps, drills, balloons, balloon catheters, and any other device considered suitable for a particular application (e.g., to treat a salivary duct).

Another optional step comprises activating the irrigation device to flush out the stone fragments. This step can be accomplished by activating a power source to introduce any suitable fluid (e.g., water, saline) into the salivary duct to assist with the removal of material (e.g., stone fragments) from the salivary duct.

Another optional step comprises removing the irrigation device from the lumen of the sheath. This step can be accomplished by applying a proximal force on any suitable portion of the irrigation device until the irrigation device is completely removed from the salivary duct and sheath.

While the various steps, alternative steps, and optional steps have been described above with respect to removing a stone disposed in a salivary duct, these steps, alternative steps, and optional steps can be accomplished with respect to treating any suitable condition within any suitable bodily passage including, but not limited to, a salivary duct, the urinary tract, and any other bodily passage considered suitable for a particular application. In addition, these steps, alternative steps, and optional steps can be included in, accomplished concurrently with, and/or accomplished in the alternative to, the methodologies, steps, alternative steps, and/or optional steps described above with respect to the exemplary method 1000 of treatment.

The foregoing detailed description provides exemplary embodiments of the invention and includes the best mode for practicing the invention. The description and illustration of embodiments is intended only to provide examples of the invention, and not to limit the scope of the invention, or its protection, in any manner.

What is claimed is:

1. A method of removing a stone disposed within a salivary duct having a salivary duct opening, the method comprising the steps of:

positioning a control handle on a medical device having a proximal end and a distal end;

releasably attaching the control handle to the medical device;

inserting the distal end of the medical device into a lumen defined by a scope having a proximal end and a distal end such that the distal end of the medical device is disposed distal to the distal end of the scope, the lumen of the scope extending between an opening at the proximal end of the scope and an opening at the distal end of the scope;

inserting the distal end of the medical device through said salivary duct opening such that the distal end of the medical device is disposed distal to said salivary duct opening and in said salivary duct;

inserting the distal end of the scope through said salivary duct opening such that the distal end of the scope is disposed distal to said salivary duct opening and in said salivary duct;

navigating the distal end of the medical device through said salivary duct and towards a point of treatment;

contacting the distal end of the medical device with said stone disposed in said salivary duct;

performing treatment using the medical device; and withdrawing the medical device from said salivary duct;

wherein the control handle comprises:

a first portion having a proximal end, a distal end, a first shaft, a projection, and defining a recess and an aperture, the shaft extending from the proximal end towards the distal end of the first portion, the projection extending from a location between the proximal end and the distal end to the distal end of the first portion, the recess extending into the projection from the distal end of the first portion towards the proximal end of the first portion to a recess base, the aperture extending from a first opening defined on the proximal end of the first portion to a second opening defined on the recess base;

a second portion having a proximal end, a distal end, a second shaft, and defining a recess and an aperture, the second shaft extending from the proximal end to the distal end of the second portion, the recess extending into the second shaft from the proximal end towards the distal end of the second portion to a recess base, the aperture extending from a first opening defined on the recess base of the second portion to a second opening defined on the distal end of the second portion; and a compressible member having a proximal end and a distal end;

wherein a portion of the compressible member is disposed within one of the recess defined by the first portion or the recess defined by the second portion;

wherein the first portion is adapted to be releasably attached to the second portion;

wherein the projection is adapted to be received by the recess defined by the second portion; and wherein said control handle is moveable between a first configuration and a second configuration, in the first configuration the projection is free of the recess of the second portion, in the second configuration the projection is disposed within the recess of the second portion and the first portion is releasably attached to the second portion.

2. The method of claim 1, wherein the compressible member defines a lumen extending from an opening on the proximal end of the compressible member to an opening on the distal end of the compressible member; and wherein the lumen of the compressible member defines a first inner diameter when the control handle is in the first configuration and a second inner diameter when the control handle is in the second configuration, the second inner diameter being less than the first inner diameter.

3. The method of claim 1, wherein the control handle further comprises a rigid member disposed adjacent the compressible member and having a proximal end and a distal end;

wherein a portion of the rigid member is disposed within one of the recess defined by the first portion or the recess defined by the second portion.

4. The method of claim 1, wherein the scope comprises a second lumen extending between an opening at the proximal end of the scope and an opening at the distal end of the scope.

5. The method of claim 1, wherein the medical device comprises a lithotripter.

6. The method of claim 5, wherein the lithotripter is selected from the group comprising pneumatic lithotripters and ultrasonic lithotripters.

7. The method of claim 1, wherein the medical device is selected from the group comprising probes, lithotripsy probes, optics, fiber optics, fibers, laser fibers, suction devices, irrigation devices, baskets, stone baskets, graspers, forceps, grasping forceps, drills, balloons, and balloon catheters.

8. The method of claim 1, wherein the step of inserting the distal end of the medical device into the lumen defined by the scope such that the distal end of the medical device is disposed distal to the distal end of the scope is performed after the step of releasably attaching the control handle to the medical device.

9. The method of claim 1, further comprising the step of inserting a sheath having a proximal end and a distal end through said salivary duct opening such that the distal end of the sheath is disposed distal to said salivary duct opening and in said salivary duct, the sheath defining a lumen that extends between an opening at the proximal end of the sheath and an opening at the distal end of the sheath;

wherein the step of inserting the distal end of the medical device through said salivary duct opening such that the distal end of the medical device is disposed distal to said salivary duct opening and in said salivary duct and the step of inserting the distal end of the scope through said salivary duct opening such that the distal end of the scope is disposed distal to said salivary duct opening and in said salivary duct comprise inserting the distal end of the medical device and the distal end of the scope through the lumen defined by the sheath such that the distal end of the medical device and the distal end of the scope are disposed distal to the distal end of the sheath.

10. The method of claim 9, wherein the distal end of the scope is advanced through the lumen defined by the sheath towards the point of treatment.

11. The method of claim 1, wherein the medical device is selected from the group consisting of probes and laser fibers.

* * * * *